Figure 1:
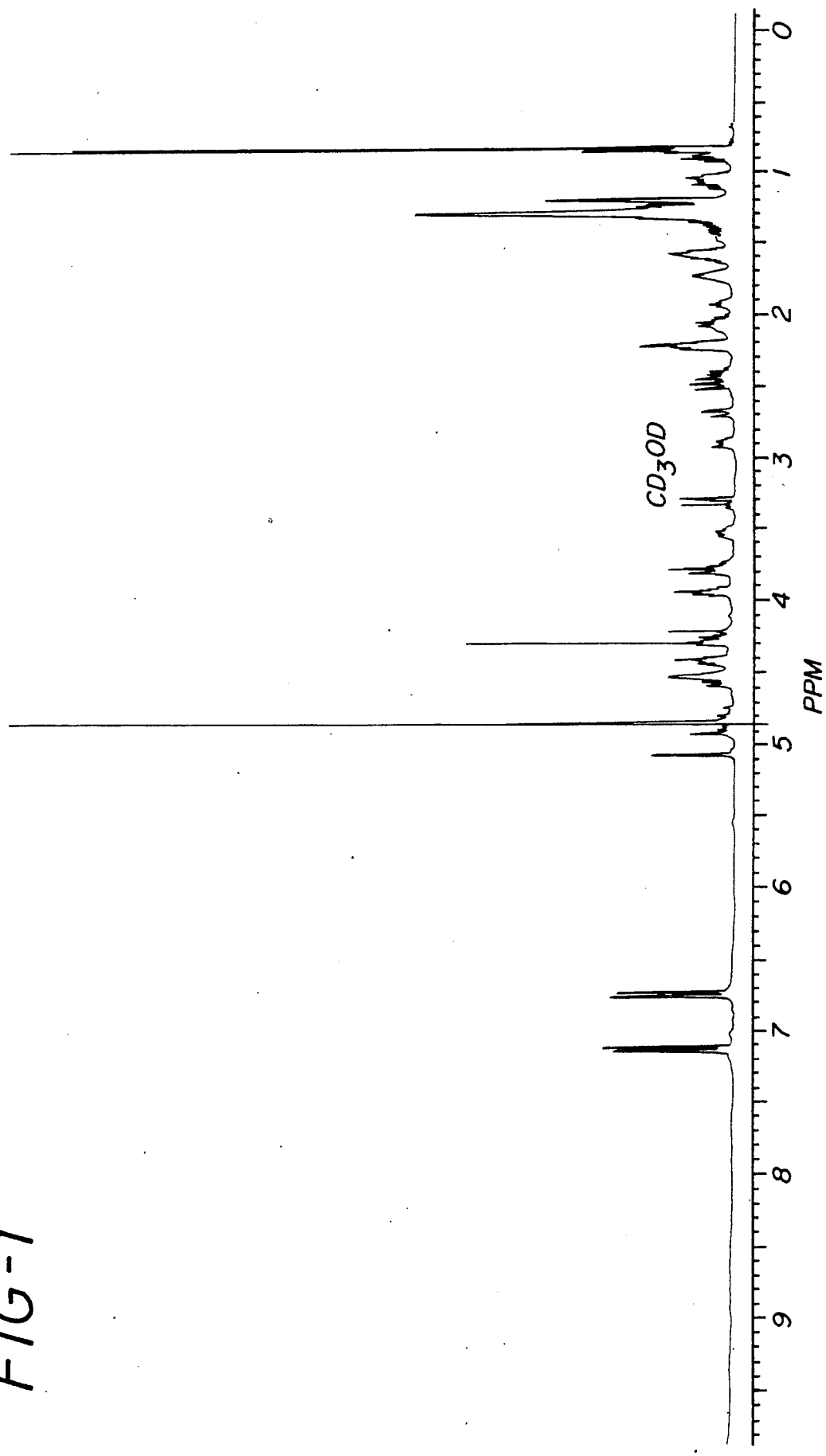

United States Patent [19]

Sesin et al.

[11] Patent Number: 5,049,546

[45] Date of Patent: Sep. 17, 1991

[54] ANTIBIOTIC AGENTS

[75] Inventors: David F. Sesin, Rahway; Jerrold M. Liesch, Princeton Junction; Jimmy M. Fountoulakis, Westfield; Prakash S. Masurekar, Warren, all of N.J.; Louis Kaplan, New City, N.Y.; Carol F. Wichmann, Westfield, N.J.

[73] Assignee: Merck & Co., Inc., Rahway, N.J.

[21] Appl. No.: 495,653

[22] Filed: Mar. 19, 1990

[51] Int. Cl.$^5$ .................... A61K 31/395; C07D 7/64; C07D 487/14

[52] U.S. Cl. .................................. 514/9; 514/183; 435/118; 435/252.1; 530/321; 540/460

[58] Field of Search .................... 514/9, 183; 530/321; 540/460

[56] References Cited

U.S. PATENT DOCUMENTS

| | | | |
|---|---|---|---|
| 3,978,210 | 8/1976 | Mizuno et al. | 424/118 |
| 4,024,245 | 5/1977 | Hoehn et al. | 424/119 |
| 4,024,246 | 5/1977 | Higgens et al. | 424/119 |
| 4,173,629 | 11/1979 | Dreyfuss et al. | 424/118 |
| 4,287,120 | 9/1981 | Abbott et al. | 530/321 |
| 4,288,549 | 9/1981 | Boeck et al. | 435/119 |
| 4,293,482 | 10/1981 | Abbott et al. | 530/321 |
| 4,293,483 | 10/1981 | Debono | 530/321 |
| 4,293,485 | 10/1981 | Debono | 530/321 |
| 4,293,487 | 10/1981 | Debono | 530/321 |
| 4,293,488 | 10/1981 | Debono | 530/321 |
| 4,293,489 | 10/1981 | Debono | 530/321 |
| 4,293,490 | 10/1981 | Abbott et al. | 530/321 |
| 4,293,491 | 10/1981 | Debono | 530/321 |
| 4,299,762 | 11/1981 | Abbott et al. | 530/321 |
| 4,299,763 | 11/1981 | Abbott et al. | 530/321 |
| 4,304,716 | 12/1981 | Abbott et al. | 530/321 |
| 4,320,053 | 3/1982 | Abbott et al. | 530/321 |
| 4,320,054 | 3/1982 | Abbott et al. | 530/321 |
| 4,322,338 | 3/1982 | Abbott et al. | 530/321 |

FOREIGN PATENT DOCUMENTS

| | | | |
|---|---|---|---|
| 57549 | 8/1977 | Belgium | 530/321 |
| 859067 | 3/1978 | Belgium | 530/321 |
| A10032009 | 7/1981 | European Pat. Off. | 530/321 |
| A20311193 | 4/1989 | European Pat. Off. | 530/321 |
| A30311194 | 4/1989 | European Pat. Off. | 530/321 |
| 2803581 | 8/1979 | Fed. Rep. of Germany | 530/321 |
| 2050385A | 1/1981 | United Kingdom | 530/321 |

OTHER PUBLICATIONS

Benz et al., Helv. Chim. Acta 57, 8, 2459–77 (1974).
Traber et al., Helv. Chim. Acta 62,4, 1252–67 (1979).
Roy et al., J. Antibiotics, XL, 3, 275–80 (1987).
Mukhopadhyay et al., J. Antibiotics, XL, 3, 281–89 (1987).
Gordee et al., J. Antibiotics XXXVII, 9, 1054–65 (1984).
Schwartz, R. E. et al., J. Antibiotics, 42, No. 2, 153 (1989).
Wichmann, C. F. et al., J. Antibiotics 42, No. 2, 168 (1989).
Fromtling, R. A. et al., J. Antibiotics, 42, No. 2, 174 (1989).
Pache, W. et al., 13th International Congress Chemotherapy (1983), PS4.8/3, Part 115, Abstract No. 10; Also Referenced in Ann. Reports in Med. Chem. 19, Sec. III, 130–131.
CRC Handbook of Antibiotic Compound, vol. IV, Part I, pp. 355–367.

*Primary Examiner*—Robert T. Bond
*Attorney, Agent, or Firm*—Alice O. Robertson; Hesna J. Pfeiffer

[57] ABSTRACT

A new antibiotic cyclic lipopeptide and a method of producing it are described. The agent has very high activity against human pathogens and is of very low mammalian toxicity.

5 Claims, 1 Drawing Sheet

ANTIBIOTIC AGENTS

DESCRIPTION OF THE INVENTION

The present invention is directed to a compound having the formula

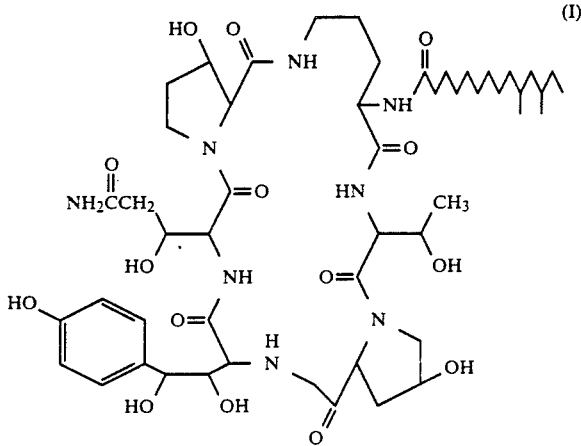

The structure of the compounds has been determined by detailed analyses of the spectral characteristics.

MASS SPECTRAL DATA

Electron impact (EI) mass spectral data were obtained either on a Finnigan-MAT MAT 212 mass spectrometer at 90 eV or Finnigan-MAT TSQ70 at 70 eV. Fast atom bombardment (FAB) spectra were recorded on a Finnigan-MAT MAT90 instrument using dithiothreitol: dithioerythritol (MB) or MB containing cesium iodide.

Compound I

Gas Chromatograph mass spectura (GC-MS) of the trimethylsilyl (TMS) derivative of the total acid hydrolysate disclosed one equivalent each of threonine, 3-hydroxyproline, 4-hydroxyproline, 3-hydroxyglutamic acid, and a C16:0 fatty acid. This compound has the molecular weight 1032 by FAB-MS (observed $[M+H]^+$ at m/z 1033; $[M+Cs]^+$ at m/z 1165). The empirical formula $C_{50}H_{80}N_8O_{15}$ was determined by high resolution FAB from the $[M+Cs]+$ ion: calculated 1032.5743, found 1032.5805.

NMR SPECTRAL DATA $^1H$ NMR Spectra were recorded at 21° C. in $CD_3OD$ at temperature on a Varian XL-400 NMR spectrometer at 400 MHz. Chemical shifts are shown in ppm relative to tetramethylsilane (TMS) at zero ppm using the solvent peak at 3.30 ppm as internal reference.

$^3C$ NMR Spectra were recorded in $CD_3OD$ at 21° C. on a Varian XL-400 spectrometer at 100 MHz. Chemical shifts are given in ppm relative to tetramethylsilane (TMS) at zero ppm using the solvent peak at 49.0 ppm as internal reference.

$^1H$ NMR obtained in $CD_3OD$ is seen in FIG. 1.

$^{13}C$ NMR Chemical Shifts ($CD_3OD$, 100 MHz): 11.57, 19.77, 20.18, 20.72, 24.23, 27.02, 27.57, 28.03, 30.27, 30.35, 30.54, 30.75, 31.11, 31.25, 32.92, 34.49, 36.74, 37.86, 38.06, 38.58, 39.86, 45.94, 46.89, 52.83, 55.59, 56.65, 57.20, 58.38, 62.47, 68.07, 69.88, 70.66, 71.27, 74.33, 75.85, 76.79, 116.2(x2), 129.6(x2), 133.1, 158.5, 169.6, 172.4, 172.6, 172.9, 173.6, 175.3, 176.1, 176.8 ppm.

On the basis of these and other data, Compound I is believed with considerable certainty to have the structure indicated.

The compound is a white solid, soluble in organic solvents such as methanol, ethanol, dimethylformamide, dimethyl sulfoxide, ethyl acetate and the like.

The compound of this invention has antifungal properties against both filamentous fungi and yeasts. It is particularly useful against organisms causing pathogenic mycotic infections such as *Candida albicans, Candida rugosa, Candida parapsilosis* and the like, where high activity is exhibited over a panel of strains of the organisms.

Moreover, unlike a number of antifungal agents, such as amphotericin B, which while active against *Candida albicans* and other fungal pathogens are limited in their ability because of the untoward and dangerous side effects, the antifungal agent of the present invention is not only a very effective but is substantially free of undesirable side reactions.

Red blood cell lysis, a harmful and potentially fatal side reaction is shown by many compounds at concentrations approaching the therapeutic dose and this property has limited the applicability of these compounds as drugs. The compounds of the present invention would require a concentration of drug far above that required for therapeutic use before red blood cell lysis could occur.

The compound is also effective antifungally against filamentous fungi, especially *Cochliobolus miyabeanus, Aspergillus* species, Penicillium species, Fusarium species, Alternaria species, Neurospora species and the like.

The compound of formula (I) are also useful as an agent for the treatment of *Pneumocystis carinii*, the causative agent of pneumonia of particular severity to immune compromised patients such as those with acquired immune deficiency syndrome (AIDS).

Compounds I is conveniently produced by cultivating *Zalerion arboricola* ATCC 20958, deposited under the Budapest Treaty in the Culture Collection of the American Type Culture Collection at 12301 Parklawn Drive, Rockville, Md. 20852.

*Zalerion arboricola* ATCC 20958 is a mutagenized form of *Zalerion arboricola* ATCC 20868. While Compounds I may be formed on the cultivation of *Z. arboricola* ATCC 20868, it is not readily detectable and is not formed in readily isolatable amounts.

The major product on the cultivation of *Z. arboricola* ATCC 20868 is Compound X

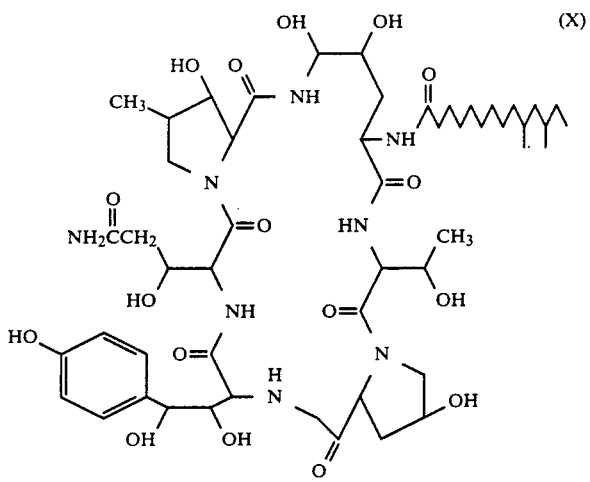

Compound X is the subject of copending application Ser. No. 362,647, filed June 7, 1989, which is a continuation of application Ser. No. 105,795 filed Oct. 10, 1987, now abandoned.

The discovery of Compound I was made possible by cultivation of *Z. arboricola* ATCC 20958. The mutant *Z. arboricola* ATCC 20958 may be produced by treating a spore suspension of *Z. arboricola* ATCC 20868 with a mutagen, followed by plating, incubating and isolating as hereinafter more fully described. Although about a hundred different mutants were obtained by the procedure, only one mutant was found to accomplish the results achieved by the present invention. This culture, which is identified in the Merck Culture Collection as MF 5405, has been deposited in the permanent culture collection of the American Type Culture Collection, 2301 Parklawn Drive, Rockville, Md. 20852 and is accessible under the accession number ATCC 20958.

For the production of the mutant, any of the agents commonly used to produce mutants such as ultraviolet radiation, chemical mutagen, or intercalating agent may be employed. Suitable chemical mutagnes include N-nitroso-N-methylurethane and N-methyl-N'-nitro-N-nitrosoguanidine.

In the present instance the *Z. arboricola* mutant was obtained by treating a spore suspension of *Z. arboricola* ATCC 20868 in 0.3M tris(hydroxymethyl)aminomethane (TRIS) buffer with N-nitroso-N-methylurethane, plating the treated suspension on potato dextrose agar and incubating to develop colonies, thereafter isolating the colonies, transferring the separate colonies to slants of potato dextrose agar and incubating for 10 to 14 days to obtain cultures of mutants of *Z. arboricola*, one of which was tentatively identified as Z1-18, subsequently maintained in the Merck Culture Collection as MF 5405, and presently available as ATCC 20958.

The colonial and morphological description of *Z. arboricola* ATCC 20958 are as follows:

Colonies on potato-dextrose agar (Difco) at 20° C. slow-growing, attaining a diameter of 8-12 mm in one week. Mature colonies (3-4 weeks) on potato-dextrose agar effuse, with submerged and aerial hyphae, surface hairy, lanose, or funiculose, dull to moderately shiny, forming raised, densely compact colonies, with a substromatic texture due to dense conidia formation. Colony color pale olive-brown, olive, olive-brown, finally olive-black, Isabella Color, Sayal Brown, Tawny-olive, Saccardo's Umber, Sepia, Brownish Olive, Raw Umber, Dark Olive, Olivaceous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1-3 um wide, thin- to slightly thick-walled, with walls smooth to slightly incrusted or verrucose. Aerial hyphae often adhering together in facicles. Setae and hyphopodia absent.

Conidiogeneous cells monoblastic, scattered to dense, intrgrated, terminal and intercalary, arising directly from undifferentiated hyphae, at right to slightly acute angles. Conidia originating as irregular chains, filaments, or coils, later developing as compact, irregular masses of 6-25 cells. Individual conidial cells, 3-6 um in diameter, globose, subglobose, or slightly irregular to lobed, smooth to finely verruculose, yellow-brown to olive brown.

Compound I is obtained by cultivating *Z. arboricola* ATCC 20958 in a suitable nutrient medium under conditions hereinafter described until a substantial amount of antifungal activity is detected in the culture medium, harvesting by extracting the active components from the fermentation medium with a suitable solvent, concentrating the solution containing the desired component, then subjecting the concentrated material to chromatographic separation to isolate Compound I from other metabolites also present in the cultivation medium.

PRODUCTION

Compound I is produced by cultivating *Z. arboricola* MF 20958 in a suitable nutrient medium containing sources of carbon and nitrogen assimilable by the microorganism and also containing low levels of inorganic salts. The medium may be supplemented with trace metals, although if complex sources of carbon and nitrogen are employed, the trace metals are usually present in the complex sources.

The sources of carbon include glycerol, sugars, sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 per cent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Although the growth medium may be prepared in a conventional manner from the foregoing nutrients, the presence of certain nutrients and/or combination of nutrients favor the production of Compound I. Thus, ammonium salts are important as an immediate source of nitrogen and monobasic potassium phosphate is important for pH control. Mannitol is especially useful in compositions, not only for enhancing the amount of desired product formed but also in improving the rate of production of the desired product.

The cultivation medium may be either liquid or solid.

Representatives suitable mannitol containing media for production of Compound I are the following:

| RG2 MEDIUM | per liter | RG120 MEDIUM | per liter |
|---|---|---|---|
| Mannitol | 44 g | Mannitol | 91 g |
| Corn Steep Liquor | 4 g | Corn Steep Liquor | 4 ml |
| Lard Water | 4 g | Lard Water | 4 g |
| Pectin | 10 g | Pectin | 10 g |
| $KH_2PO_4$ | 2 g | $KH_2PO_4$ | 2 g |
| Tomato Paste | 4 g | Tomato Paste | 4 g |
| Peptonized Milk | 4 g | Peptonized Milk | 4 g |
| Glycine | 2 g | Glycine | 2 g |
| Peanut Meal | 4 g | Peanut Meal | 4 g |
| pH adjusted to 7.0 | | pH adjusted to 7.0 | |
| TG102 MEDIUM | per liter | TG103 MEDIUM | per liter |
| D-Mannitol | 40 g | D-Mannitol | 40 g |
| Bacto-Peptone* | 33 g | Bacto-Peptone* | 33 g |
| Bacto-Yeast Extract | 10 g | Bacto-Yeast Extract | 10 g |
| $(NH_4)_2SO_4$ | 5 g | $(NH_4)_2SO_4$ | 5 g |
| $KH_2PO_4$ | 9 g | $KH_2PO_4$ | 9 g |
| no pH adjustment | | no pH adjustment | |

*Casein hydroysate-Humko Sheffield, Memphis, Tenn.

Other media which favor the production of the compounds of formula I are those with contain D-mannitol as carbon source, peptonized milk as the complex nitrogen source, glycine as amino acid and a buffer, and preferably containing lactic acid, trace elements and vegetable oil selected from, soy, peanut and sunflower oils, has been the most satisfactory. The useful ranges for the components are as follows:

| | grams/liter |
|---|---|
| D-mannitol | 20–100 |
| $KH_2PO_4$ | 0.5–3 |
| glycine | 1–4 |
| Peptonized milk | 2–20 |
| Lactic acid | 0–3 |
| Trace element mixture | 0–15 ml |
| Vegetable oil (soy, peanut, sunflower) | 0–20 |
| pre-sterilization pH = 7 | |
| Trace elements | per liter 0.6NHCl |
| $FeSO_4.7H_2O$ | 1.0 g |
| $MnSO_4.4H_2O$ | 1.0 g |
| $CuCl_2.2H_2O$ | 0.025 g |
| $CaCl_2$ | 0.1 g |
| $H_3BO_3$ | 0.056 g |
| $(NH_4)_6Mo_7O_{24}.H_2O$ | 0.019 g |
| $ZnSO_4.7H_2O$ | 0.2 g |

Specific media include:

| S2 MEDIUM | per liter | S6 MEDIUM | per liter |
|---|---|---|---|
| D-Mannitol | 44 g | D-Mannitol | 44 g |
| $KH_2PO_4$ | 2 g | $KH_2PO_4$ | 2 g |
| Glycine | 2 g | Glycine | 2 g |
| Peptonized Milk | 15 g | Peptonized Milk | 15 g |
| Lactic acid | 2 g | Lactic acid | 10 ml |
| Trace Elements | 10 ml | Trace Elements | 10 g |
| | | Soybean oil | 10 g |
| pH 7.0 (pre-sterilization) | | pH 7.0 (pre-sterilization) | |

Representative of useful solid media are the following:

| | per 250 ml flask | Base liquid | per liter |
|---|---|---|---|
| F204 SOLID MEDIUM | | | |
| Millet | 15 g | Ardamine PH (**) | 33.0 g |
| Base liquid | 15 ml | Sodium Tartrate | 6.6 g |
| | | $FeSO_4.7H_2O$ | 0.66 g |
| | | Monosodium Glutamate | 6.6 ml |
| | | Corn oil | 6.6 ml |
| | | no pH adjustment | |
| F4-SF SOLID MEDIUM | | | |
| Cracked corn | 15 g | Ardamine PH | 0.2 g |
| Base liquid | 10 ml | $H_2PO_4$ | 0.1 g |
| | | $MgSO_4.7H_2O$ | 0.1 g |
| | | Sodium Tartrate | 0.1 g |
| | | $FeSO_4.7H_2O$ | 0.01 g |
| | | $ZnSO_4.7H_2O$ | 0.01 g |
| | | no pH adjustment | |

**Yeast autolysate available from Yeast Products Inc. Clifton, New Jersey

Employing one of the foregoing or similar medium, the fermentation may be carried out by first inoculating a nutrient seed medium, with a previously thawed vegetative mycelia of *Z. arboricola* ATCC 20958, and the inoculated medium incubated for at least 3 days to produce organisms which serve as seeds in the production of the compounds of formula (I). The seed medium is generally in the pH range of 5 to 8.1, optimally 6 to 7.5. A representative seed medium is one of the following composition:

| Seed Medium (KF Medium) | |
|---|---|
| | per liter |
| Corn Steep liquor | 5.0 g |
| Tomato paste | 40.0 g |
| Oat flour | 10.0 g |
| Glucose | 10.0 g |
| Trace elements* | 10.0 ml |
| Distilled water | 1000 ml |
| pH 6.8 | |

*Previously given

In carrying out the process, a slant section of a preserved culture of ATCC 20958 is inoculated into an appropriate seed medium and the flasks incubated with or without agitation at temperatures in the range of from about 15° C. to about 30° C. for from 2 to 30 days, preferably 20° C. to 28° C. for 2 to 14 days. Agitation when employed is preferably about 200 to 220 rpm but may be up to 400 rpm when growth is abundant, usually between 2 and 5 days, the growth may be used to inoculate the production medium for the production of the compounds of this invention. Preferably however, a second stage fermentation is carried out, inoculating with a portion of the culture growth and then employing similar conditions but generally with a shortened incubation period of about 1 to 3 days. The growth then is employed to inoculate the production medium.

The fermentation production medium inoculated with the culture growth is incubated for 3 to 30 days, usually 7 to 14 days, with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°-28° C. are most preferred. The pH of the nutrient medium suitable for producing the instant compounds can vary from about 5.0 to 8.5 with a preferred range of from about 6.0 to 7.5. After the appropriate period for the production of the desired compound or compounds, the latter is recovered from the fermentation medium as hereinafter more fully described.

HARVEST AND ISOLATION

After completion of the cultivation, Compound I is harvested and isolated from the medium. The exact steps may vary somewhat on whether the fermentation is carried out in liquid or solid medium.

When the fermentation is carried out on a solid medium, the first step may be adding an alcoholic solvent to the fermentation medium, thoroughly mixing, then filtering, recovering and concentrating the aqueous alcohol filtrate. The concentrated filtrate may be first back-extractd or washed with a lower aliphatic hydrocarbon solvent such as hexane or other alkane to remove alkane soluble impurities. The alkane washed filtrate may be extracted or partitioned with a water-immiscible oxygenated organic solvent and the resulting solution concentrated, then placed onto a column for at least one, generally several chromatographic separation steps. Suitable columns are silica gel, reverse phase resin and "Sephadex" LH-20 (dextran adsorbent, Pharmacia).

When the fermentation is carried out in a liquid medium, in one method, the mycelial solids are filtered and recovered from the fermentation medium. Alcohol is added to the mycelial cake, and the mycelial solid thoroughly mixed with the alcohol, filtered, and the filtrate collected and concentrated. In an alternative method, the whole broth can be extracted by the addition of one volume of alkanol, preferably methanol, and filtered to remove solid impurities. The alkanol extract is then absorbed on "Diaion" HP-20 (Mitsubishi Chemical Industries, Ltd) resin and eluted with 100% alkanol. "Diaion" SP-207 (brominated) or other commercially available styrene-divinylbenzene copolymer also may be employed. A second dilution/HP-20 adsorption/elution step is utilized to concentrate the sample in preparation for chromatographic separations. Sometimes, a third dilution/HP-20 adsorption/elution step may be desirable for volume reduction.

The alcoholic solvent to be employed in the initial extraction of the active agent from the solid nutrient medium or from the mycelial pad may be any of the lower alcohols such as methanol, ethanol, isopropanol, and the like. Methanol is preferred.

If the active agent is partitioned from the aqueous alkanol or aqueous methanol solution, then suitable solvents are esters, such as ethyl acetate, isopropyl acetate, butyl acetate, or ketones, such as methyl ethyl ketone.

The chromatographic separation may be carried out by employing conventional column chromatography with non-ionic resin or by high performance liquid chromatography employing reverse phase resin. The fractions containing the antibiotic Compound I may be detected by antifungal assay using *Candida albicans*. Generally, more than one chromatographic separation steps are employed. In a most preferred procedure, one or more separations are carried out employing column chromatography and a final separation is carried out employing high performance liquid chromatography (HPLC) with $C_{18}$ reverse phase resin.

When conventional column chromatography is employed for chromatographic separations, silica gel is the preferred adsorbent. Usually more than one chromatographic separation is employed. Silica gel may be used in all the separations while employing different eluting agents. However, it may be combined advantageously with the use of a different adsorbent such as a dextran adsorbent sold under the trade name of "Sephadex" LH-20. Other adsorbents such as alumina, styrene-divinylbenzene copolymers available commercially as "Diaion" HP-20, HP-30, HP-40, SP-207 and "Amberlite" XAD-2, XAD-2, XAD-4, XAD-16 (Rohm and Haas Co.) also may be employed.

In the fractionation and recovery of the active component by chromatography on silica gel, ester/alcohol mixtures with increasing concentration of alcohol provide good separations. A mixture of ethyl acetate and methanol has been found to be especially useful. These may be employed in isocratic, step gradient or continuous gradient systems. When a dextran adsorbent such as "Sephadex" LH-20, is employed, a chlorohydrocarbon/hydrocarbon/alcohol solvent system may be employed. A mixture of methylene chloride/hexane/methanol has been found to be especially useful.

In carrying out the HPLC separation, the alcohol solution containing material recovered from the conventional chromatography is concentrated and the residue dissolved in methanol/water in the same ratio as found in the mobile phase and placed on a column packed with commercial reverse phase resin or on a column filled with silica gel/$C_{18}$ reverse phase resin prepared as amply reported in the literature. Alternatively, the alcohol solution may be diluted to 50 percent with water and pumped onto the column. The column is washed using methanol/water 1:1 and eluted with higher proportions of methanol at 800-2000 psi which produces a flow rate of about 20 ml/min. Separation is monitored at 210 nm.

The fractions are assayed for activity with *Candida albicans*. The product is recovered from any of the chromatographic procedures by combining the *Candida albicans* active fractions and concentrating under reduced pressure.

Compound I is active against many fungi, and also against *Pneumocystis carinii*.

The antifungal properties may be illustrated with the minimum fungicidal concentration (MFC) determinations against certain Candida organisms in a microbroth dilution assay carried out in Yeast Nitrogen Base (Difco) with 1 percent dextrose (YNBD). In carrying out the assay, Compound I was solubilized in 10 percent dimethyl sulfoxide (DMSO) and diluted to 2560 $\mu$g/ml. The compound was then diluted to 256 $\mu$g/ml in YNBD. 0.15 ml of the suspension was dispensed to the top row of a 96-well plate (each well containing 0.15 ml of YNDB) resulting in a drug concentration of 128 $\mu$g/ml. Two-fold dilutions were then made from the top row to obtain final drug concentratons ranging from 128 to 0.06 $\mu$g/ml.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5\times10^6$ colony forming units (CFU)/ml.

96-well microplates were inoculated using a MIC-2000 (Dynatech) which delivers 1.5 µl per well yielding a final inoculum per well of $1.5-7.5\times10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 µl samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot. The results are seen in the following table:

| Fungi Strain No. | Minimum Fungicidal Concentration (µg/ml) I |
|---|---|
| *Candida albicans* | |
| MY 1055 | 32 |
| MY 1585 | 32 |
| MY 1208 | 32 |
| MY 1028 | 16 |
| MY 1750 | 16 |
| MY 1783 | 16 |
| *Candida tropicalis* | |
| MY 1012 | 32 |
| *Candida parapsilosis* | |
| MY 1009 | 128 |
| MY 1010 | 64 |

Compound I is useful for inhibiting or alleviating *Pneumocystis carinii* infections. In a representative study, the effectiveness of Compound I in rats were determined. Sprague-Dawley rats (weighing approximatley 150 g) were immunosuppressed with dexasone in the drinking water (2 mg/ml) and maintained on a low protein diet for 6 weeks to induce the development of pneumocystis pneumonia from a latent infection. Before drug treatment 3 rats were sacrificed to confirm the presence of *Pneumocystis carinii* pneumonia (PCP); all three rats had infections. A group of 5 rats were injected twice daily for five days intraperitioneally with compound in 0.5 ml of vehicle (10% DMSO in water). The control group of 5 rats received vehicle alone. All animals continued to receive dexasone in the drinking water and low protein diet during the drug treatment period. At the completion of treatment all animals were sacrificed, the lungs were removed and processed, and the extent of disease determined by microscopic analysis of stained slides. The results of this study show that Compound I had good antipneumocystis activity with an $ED_{90}$ of $\leq 1.0$ mg/kg.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent of weight of Compound I. Concentrate compositions suitable for dilutions prior to use may contain 90 percent or more by weight. The compositions include compositions suitable for oral, rectal, topical, parenteral (including subcutaneous, intramuscular, and intravenous), pulmonary (nasal or buccal inhalation), nasal administration, or insufflation. The compositions may be prepacked by intimately mixing Compound I with the components suitable for the medium desired.

When the compound is for antifungal use any method of administration may be used. For treating mycotic infection oral administration is frequently preferred. When oral administration is to be employed, it may be with a liquid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound I also may be formulated in therapeutic compositions for intravenous or intraperitoneal injection and may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending stabilizing and/or dispersing agents. Buffering agents as well as additives such as saline or glucose may be added to make the solutions isotonic. The drug also may be solubilized in alcohol/propylene glycol or polyethyleglycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of Compound I in suitable propellants, such as fluorocarbons or hydrocarbons.

Another method of administration is insufflation, particularly if the infection has spread to the ears and other body cavities.

If the application is to be topical, the drug may be formulated in conventional creams and ointments such as white petrolatum, anhydrous lanolin, cetyl alcohol, cold cream, glyceryl monostearate, rose water and the like. Usually a 1 to 2 percent cream solution is prepared and applied to the area to be treated.

The following examples illustrate the invention but are not to be construed as limiting.

EXAMPLE I

A. Preparation of Mutant Z. arboricola ATCC 20958

A culture of Z. arboricola ATCC 20868 was grown on potato dextrose agar in petri plates at 25° C. for 3 weeks. 10 milliliters of 0.3M TRIS buffer, pH 7, was added to the plates and the spores scraped off the surface into the buffer with a sterile cotton swab. The suspension in the buffer was decanted off and the procedure repeated twice. The spore suspensions were combined and filtered through glass wool to remove large clusters of spores. The filtrate was centrifuged at first at 600 rpm then at 700 rpm and finally at 800 rpm, each time for 3 minutes with the pellet being discarded after each centrifugation. The supernatant from the third centrifugation was then centrifuged at 3000 rpm for 5 minutes. The pellet from this centrifugation was resuspended in 3 milliliters of 0.3M TRIS buffer, pH 7, and used for mutagenic treatment. This suspension contained from $10^3$ to $10^4$ spores per milliliter.

To the spore suspension was added 50 μg/ml of N-nitroso-N-methylurethane and the resulting mixture shaken at 300 rpm for 20 minutes at room temperature. At the end of this period, the mixture was centrifuged and the supernatant liquid was removed. The pellet was washed twice with 0.3M TRIS buffer pH 7.0 and then resuspended in the same buffer and after appropriate dilution plated on potato dextrose agar for forming isolated colonies. The plates were incubated at 25° C. for two weeks for colony formation. The colonies were isolated by separately transferring to slants of potato dextrose agar. The inoculated slants were incubated at 25° C. for 10-14 days and a plug from the slants taken and tested for the production of Compound X and other components by HPLC assay. A plug from one of the slants initially designated as Z1-18, and subsequently placed in the Merck Culture Collection as MF 5405 and thereafter deposited with the American Type Culture Collection and assigned ATCC 20958, was employed in fermentation to produce Compound I as hereinafter described.

EXAMPLE II

A suspension of spores from a slant culture of MF 5405 was inoculated into a 250 milliliter Erlenmeyer flask containing 54 milliliters of KF seed medium (previously detailed) which had been sterilized for 20 minutes at 121° C. and 15 psi.

The inoculated seed flask was incubated at 25° C. with shaking at 220 rpm for 96 hours. At the end of this time 7 milliliters of this culture were transferred to a 2-liter flask containing 500 milliliters of the seed medium. The flask was cultivated at 25° C. with shaking at 220 rpm for another 96 hours. At this time, 10 milliliters of the culture was transferred to another 2-liter Erlenmeyer flask containing 500 milliliters of seed medium and this flask was incubated at 25° C. with shaking at 200 rpm for 72 hours. Then, the entire contents of the flask was transferred to a 22-liter bioreactor containing 15 liters of production medium of the following composition (expressed in grams per liter): mannitol, 40.0; NZ amine (Type E), 33.0; yeast extract (Fidco), 10.0; $(NH_4)_2SO_4$, 5.0; $KH_2PO_4$, 9.0 and P2000 (polyethylene glycol, Dow Chemical); 2.0 milliliters. The medium was sterilized without adjusting the pH at 122° C. and 15 psi for 30 minutes. The pH of the medium after sterilization was 6.6.

The inoculated medium was then cultivated at 25° C., with agitation at 300 rpm, air flow of 4.5 liters per minute and a back pressure of 5 psi. After 165 hours, the fermentation broth was harvested for product recovery.

The fermentation broth was extracted by stirring overnight with an equal volume of methanol. The methanol extract was filtered through a 1-inch bed of celite and the filtrate adsorbed onto a 4-liter "Diaion" SP-207 column. The column was washed with 65 percent aqueous methanol and Compound I eluted with 100 percent methanol. The eluant fractions were checked for the presence of Compound I by using HPLC assay ("Zorbax" RP-18 analytical column, 4.6 mm×25 cm; 50/50 acetonitrile/water; retention time=11.7 minutes). The rich cuts, which amounted to 0.96 gram of Compound I, were combined and diluted with distilled water to a final concentration of 50 percent aqueous methanol and adsorbed onto a "Diaion" HP-20 column. The column was washed with 65 percent aqueous methanol and eluted with 100 percent methanol. The eluants were monitored for the presence of Compound I using the same HPLC assay method. The cuts rich in Compound I were combined, concentrated to dryness under vacuum and chromatographed on a 4 liter preparative liquid chromatography column using a linear gradient (50/50 methanol/water to 100 percent methanol over a 1 hour period). The fractions were checked for the presence of Compound I and the rich cuts combined and further purified on a semi-preparative RP-18 LC column ("Zorbax" 2.54 cm×25 cm; 70/30 methanol/water). The product thus obtained of greater than 95 percent purity was employed to determine the NMR spectra and mass spectrum for the compound and to obtain the values previously set forth.

EXAMPLE III 1000 compressed tablets, each containing 500 milligrams of Compound I are prepared from the following formulation:

| Compound | Grams |
| --- | --- |
| Compound I | 500 |
| Starch | 750 |
| Dibasic calcium phoshate hydrous | 5000 |
| Calcium stearate | 2.5 |

The finely powered ingredients are mixed well and granulated with 10 percent starch paste. The granulation is dried and compressed into tablets.

EXAMPLE IV 1000 hard gelatin capsules, each containing 500 milligrams of Compound I are prepared from the following formulation:

| Compound | Grams |
| --- | --- |
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE V 250 milliliters of an injectable suspension are prepared by conventional procedures having the following formulation:

| 5% DMSO/water | 250 milliliters |
| --- | --- |
| Compound I | 400 milligrams |

The ingredients are blended and thereafter sterilized for use.

EXAMPLE VI

An ointment suitable for topical application may be prepared by intimately dispersing 13 milligrams of Compound I in 1 gram of commercially available polyethylene/hydrocarbon gel.

EXAMPLE VII

An aerosol composition may be prepared having the following formulation

| | Per canister |
| --- | --- |
| Compound I | 24 mg |
| Lecithin NF, liquid concentrate | 1.2 mg |
| Trichlorofluoromethane | 4.025 g |
| Dichlorodifluoromethane | 12.15 g |

What is claimed is:

1. A compound having the formula

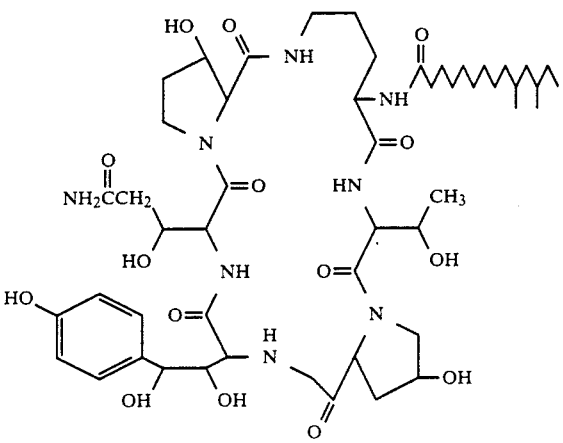

2. A method for the treatment of or for the prevention of *Pneumocystis carinii* infections in mammals which comprises administering to mammals an anti-infective amount of the compound of claim 1.

3. A method for inhibiting fungal growth comprising applying to the area where growth is to be controlled an antifungally effective amount of the compound of claim 1.

4. An antimicrobial composition comprising a compound of claim 1 in admixture with a biologically inert carrier.

5. A composition according to claim 4 in which the carrier is a pharmaceutically acceptable carrier.

* * * * *